(12) United States Patent
Little et al.

(10) Patent No.: US 6,364,839 B1
(45) Date of Patent: Apr. 2, 2002

(54) ULTRASOUND DIAGNOSTIC INSTRUMENT HAVING SOFTWARE IN DETACHABLE SCANHEAD

(75) Inventors: Blake W. Little, Bothell; Leo R. Catallo, Mercer Island; Jens U. Quistgaard, Seattle, all of WA (US)

(73) Assignee: SonoSite, Inc., Bothell, WA (US)

( * ) Notice: Subject to any disclaimer, the term of this patent is extended or adjusted under 35 U.S.C. 154(b) by 0 days.

(21) Appl. No.: 09/564,601

(22) Filed: May 3, 2000

Related U.S. Application Data

(60) Provisional application No. 60/132,421, filed on May 4, 1999, provisional application No. 60/132,558, filed on May 5, 1999, and provisional application No. 60/132,515, filed on May 4, 1999.

(51) Int. Cl.⁷ ............................................... A61B 8/14
(52) U.S. Cl. ..................................................... 600/459
(58) Field of Search ........................ 600/437, 440–447, 600/450–459; 73/625, 626; 439/374

(56) References Cited

U.S. PATENT DOCUMENTS

| | | | |
|---|---|---|---|
| 4,972,838 A | 11/1990 | Yamazaki | 128/661.09 |
| 5,235,984 A | 8/1993 | D'Sa | 128/660.07 |
| 5,690,114 A | 11/1997 | Chiang et al. | 128/661.01 |
| 5,888,087 A * | 3/1999 | Hanson et al. | 439/374 |
| 5,891,041 A | 4/1999 | Shinomura et al. | |
| 6,063,030 A * | 5/2000 | Vara et al. | 600/437 |

* cited by examiner

*Primary Examiner*—Marvin M Lateef
*Assistant Examiner*—Ali M. Imam
(74) *Attorney, Agent, or Firm*—Townsend and Townsend and Crew LLP; Henry K. Woodard

(57) ABSTRACT

An ultrasound diagnostic instrument includes a console having electronic circuitry for processing electrical signals for display including a digital processor and a memory for storing software for use with the processor, and a first connector coupled to the memory and processor. A transducer scanhead for generating ultrasound waves and receiving reflected ultrasound waves is connected through a cable and a second connector to the first connector and to the digital processor. A second memory external to the console is provided for communicating with the digital processor through the second connector, the second memory storing software and data necessary for use of the transducer scanhead in the ultrasound diagnostic instrument. The second memory can be provided in the transducer scanhead or in the second connector and can include operational data unique to the transducer scanhead, operational software for executing unique functions with the transducer scanhead, and updates and upgrades of system executable code that resides in memory within the console, thereby obviating the need for manual field upgrade or system swap when a new function, application, or transducer scanhead is required.

19 Claims, 3 Drawing Sheets

ULTRASOUND DIAGNOSTIC INSTRUMENT HAVING SOFTWARE IN DETACHABLE SCANHEAD

This invention claims priority from Provisional Application 60/132,421 filed May 4, 1999 and is related to co-pending Provisional Application 60/132,558 filed May 5, 1999 for Low Power Portable Ultrasound Diagnostic Instrument and Provisional Application 60/132,515 filed May 4, 1999 for Mobile Ultrasound Diagnostic Instrument and Docking Stand.

BACKGROUND OF THE INVENTION

This invention relates generally to medical ultrasonic diagnostic systems, and more particularly this invention relates to ultrasonic diagnostic instruments which employ detachable ultrasound transducer scanheads.

Modern ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc., were smaller desktop units about the size of a personal computer. However, such instruments lack many of the advanced features of today's premium ultrasound systems such as color Doppler imaging and three dimensional display capabilities. As ultrasound systems become more sophisticated they also become bulkier.

Disclosed in U.S. Pat. No. 5,722,412 is a diagnostic ultrasound instrument which exhibits many of the features of a premium ultrasound system in an hand-held unit. The instrument can be produced as a single unit or in a preferred embodiment the instrument is a two-part unit one including a transducer, beamformer, and image processor and the other including a display and power source for both units. In such a configuration the transducer/processor unit can be manipulated with one hand while a cable between the two units enables the video to be shown on the display unit while the lateral unit is held or positioned for optimal viewing of the ultrasound image. The cable also provides energy for the transducer/processor unit from the display unit.

Co-pending application Ser. No. 19162-3 discloses a portable ultrasound diagnostic instrument in which a power monitor and control function are incorporated to limit power consumption. Co-pending application Ser. No. 19162-8 discloses a docking stand which can be employed with the instrument of Ser. No. 19162-3.

Heretofore, the operating software and any special function software have been stored in memory with the system processor in a console of the instrument. Since various special application scanheads can be used with the instrument, the operating software for implementing the special applications has been stored in the console, thus necessitating a large memory. This can be inconvenient when new scanheads are introduced or when system software is upgraded since the console often must be returned to a central service facility for software update or the expense of having trained field personnel is required for field upgrade.

The present invention is directed to facilitating software update and special operating software without the need for a large module memory or for module retrofitting at a centralized service facility.

SUMMARY OF THE INVENTION

The present invention overcomes limitations in the prior art by providing memory in association with the transducer scanhead separate from the console of an ultrasound diagnostic instrument with the memory providing transducer specific data required for system setup, drive, and data image with transducers for various applications, and depths, and optimization settings that are unique for each. The external memory also provides a means to update and upgrade the system executable code and thereby allow the use of future transducer scanheads and to provide for future applications of the instrument. By so providing a memory outside of the console, manual field upgrade or system swap is obviated when a new function, application, or transducer scanhead is introduced.

The invention and objects and features thereof will be more readily apparent from the following detailed description and appended claims when taken with the drawings.

DETAILED DESCRIPTION OF ILLUSTRATIVE EMBODIMENTS

Figure 1:
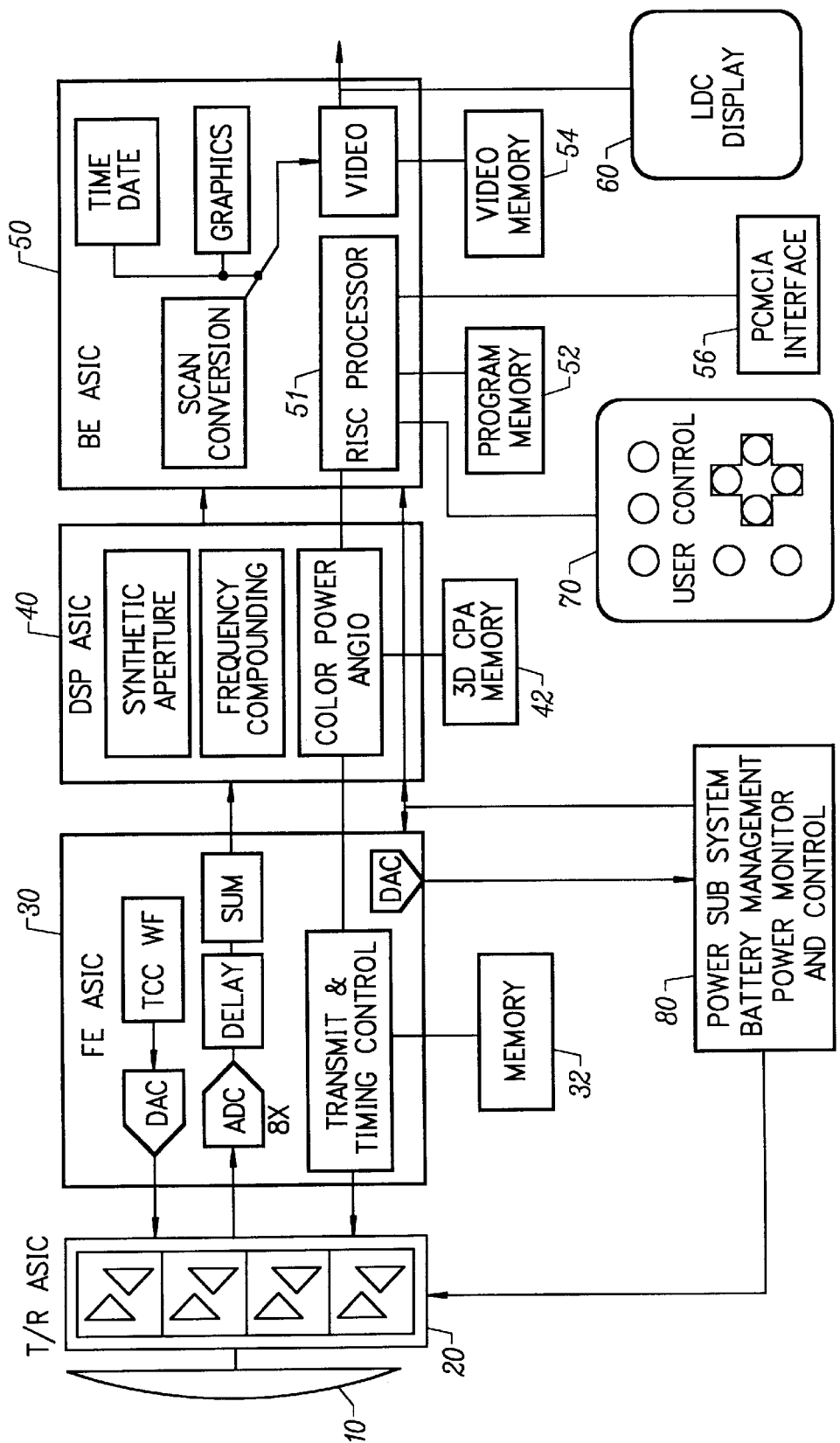
FIG. 1 is a functional block diagram of an ultrasonic diagnostic instrument as disclosed in application Ser. No. 19162-3.

FIG. 1 is a detailed functional block diagram of an ultrasonic diagnostic instrument as disclosed in co-pending application Ser. No. 19162-3. The instrument is described in more detail in U.S. Pat. No. 5,722,412, which is incorporated herein by reference. In this instrument a transducer array 10 is used for a solid state, electronic control capabilities, variable aperture, image performance and reliability. Either a flat or curved linear array can be used. In a preferred embodiment the array is a curved array, which affords a broad sector scanning field. While the preferred embodiment provides sufficient delay capability to both steer and focus a flat array such as a phased array, the geometric curvature of the curved array reduces the delay requirements on the beamformer. The elements of the array are connected to a transmit/receive ASIC 20 which drives the transducer elements and receives echoes received by the elements. The transmit/receive ASIC 30 also controls the transmit and receive apertures of the array 10 and the gain of the received echo signals. The transmit/receive ASIC is preferably located within inches of the transducer elements, preferably in the same enclosure, and just behind the transducer.

Echoes received by the transmit/receive ASIC 20 are provided to the adjacent front end ASIC 30, which beamforms the echoes from the individual transducer elements into scanline signals. The front end ASIC 30 also controls the transmit waveform, timing, aperture and focusing. In the illustrated embodiment the front end ASIC 30 provides timing signals for the other ASICs, time gain control, and monitors and controls the power applied to the transducer array, thereby controlling the acoustic energy which is applied to the patient and minimizing power consumption of the unit. A memory device 32 is connected to the front end ASIC 30, which stores data used by the beamformer.

Beamformer scanline signals are coupled from the front end ASIC 30 to the adjacent digital signal processing ASIC 40. The digital signal processing ASIC 40 filters the scanline signals and in the preferred embodiment also provides several advanced features including synthetic aperture formation, frequency compounding. Doppler processing such as power Doppler (color power angio) processing, and speckle reduction.

The ultrasound B mode and Doppler information is then coupled to the adjacent back end ASIC 50 for scan conversion and the production of video output signals. A memory device 42 is coupled to the back end ASIC 50 to provide storage used in three dimensional power Doppler (3D CPA) imaging. The back end ASIC also adds alphanumeric information to the display such as the time, date, and patient identification. A graphics processor overlays the ultrasound image with information such as depth and focus markers and cursors. Frames of ultrasonic images are stored in a video memory 54 coupled to the back end ASIC 50, enabling them to be recalled and replayed in a live realtime sequence. Video information is available at a video output in several formats, including NTSC and PAL television formats and RGB drive signals for an LCD display 60 or a video monitor.

The back end ASIC 50 also includes the central processor for the ultrasound system, a RISC (reduced instruction set computer) processor. The RISC processor is coupled to the front end and digital signal processing ASICs to control and synchronize the processing and control functions throughout the hand-held unit. A program memory 52 is coupled to the back end ASIC 50 to store program data which is used by the RISC processor to operate and control the unit. The back end ASIC 50 is also coupled to a data port configured as a PCMCIA interface 56. This interface allows other modules and functions to be attached to the hand-held ultrasound unit. The interface 56 can connect to a modem or communications link to transmit and receive ultrasound information from remote locations. The interface can accept other data storage devices to add new functionality to the unit, such as an ultrasound information analysis package.

The RISC processor is also coupled to the user controls 70 of the unit to accept user inputs to direct and control the operations of the hand-held ultrasound system.

Power for the hand-held ultrasound system in a preferred embodiment is provided by a rechargeable battery. Battery power is conserved and applied to the components of the unit from a power subsystem 80. The power subsystem 80 includes a DC converter to convert the low battery voltage to a higher voltage which is applied to the transmit/receive ASIC 20 to drive the elements of the transducer array 10. In order to limit power consumption, the power monitor and control unit 80 controls the operating mode of the LCD display 60 and video circuitry in unit 50 along with the clock frequency of the RISC processor in unit 50 and the clock frequencies of the DAC and ADC units in beamformer circuitry 30. The color angiography function unit and 3D signal processing DSP unit 40 are similarly controlled by the power monitor and control.

Figure 2:
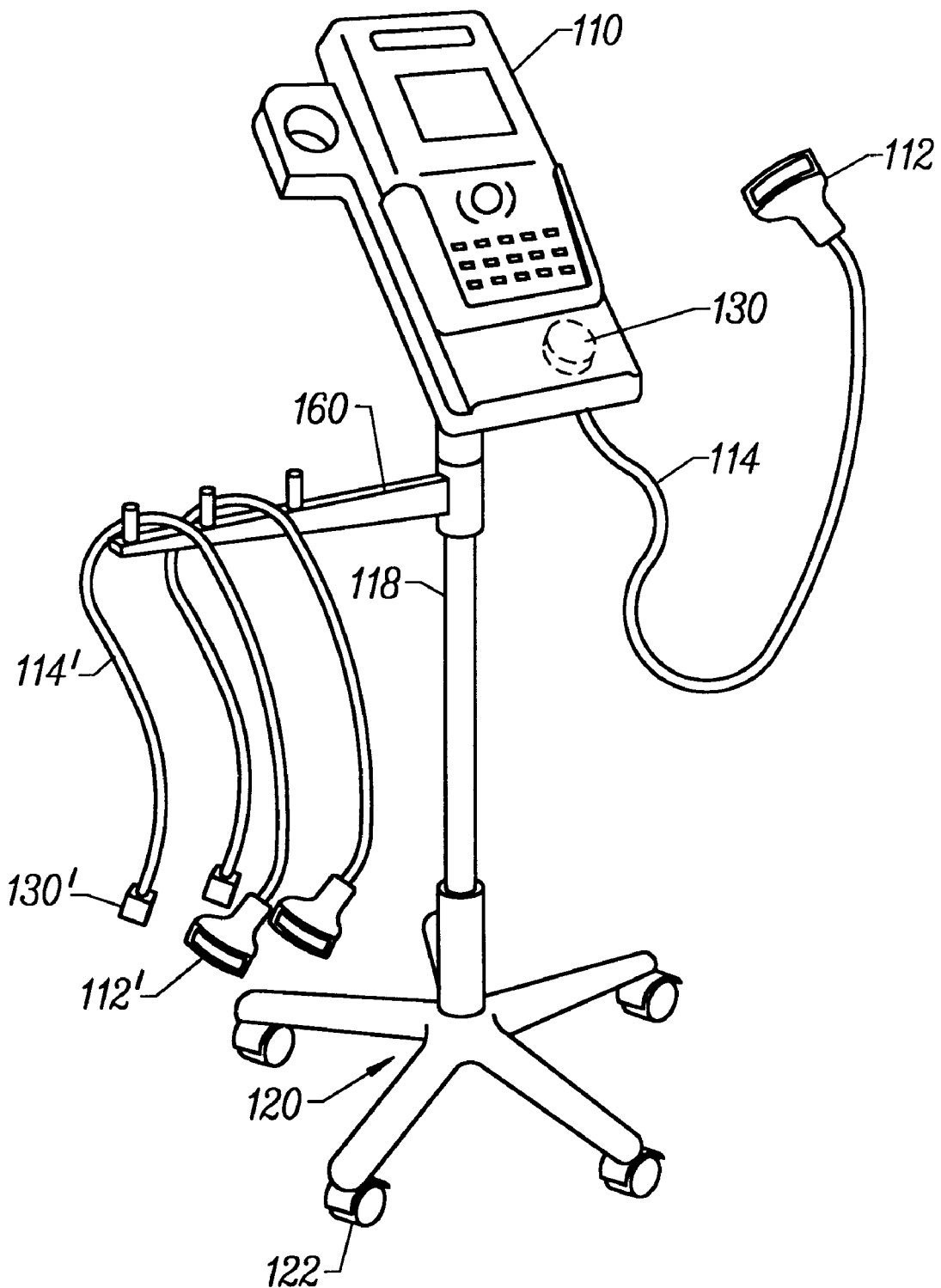
FIG. 2 is a perspective view illustrating an ultrasound diagnostic instrument and docking stand as disclosed in application Ser. No. 19162-8.

FIG. 2 is a perspective view of a mobile ultrasound diagnostic instrument and docking stand as disclosed in application Ser. No. 19162-8. The diagnostic instrument includes a console 110 and transducer scanhead 112 which is connected to console 110 through cable 114. The instrument can be of the type disclosed in U.S. Pat. No. 5,722,412 and in co-pending application Ser. No. 19162-3, as illustrated in FIG. 1.

Console 110 is received within a sleeve receptacle 116 which is supported in a raised position by means of a vertical support 118 that mounts to a base 120 having a plurality of wheels 122 for movement. Cable 114 connects a scanhead 112 to console 110 and includes a connector 130 which plugs into console 110. Alternatively, scanhead 112 can communicate with console 112 by wireless transmission of signals from a transceiver in the scanhead to and from a transceiver in console 112.

In using the instrument of FIG. 2 it is often expeditious to connect any one of a plurality of scanheads 112 to the console for specific applications. Arm 160 is attached to the vertical support 118 for receiving a plurality of scanheads 112', cables 114', and connectors 130'.

Figure 3:
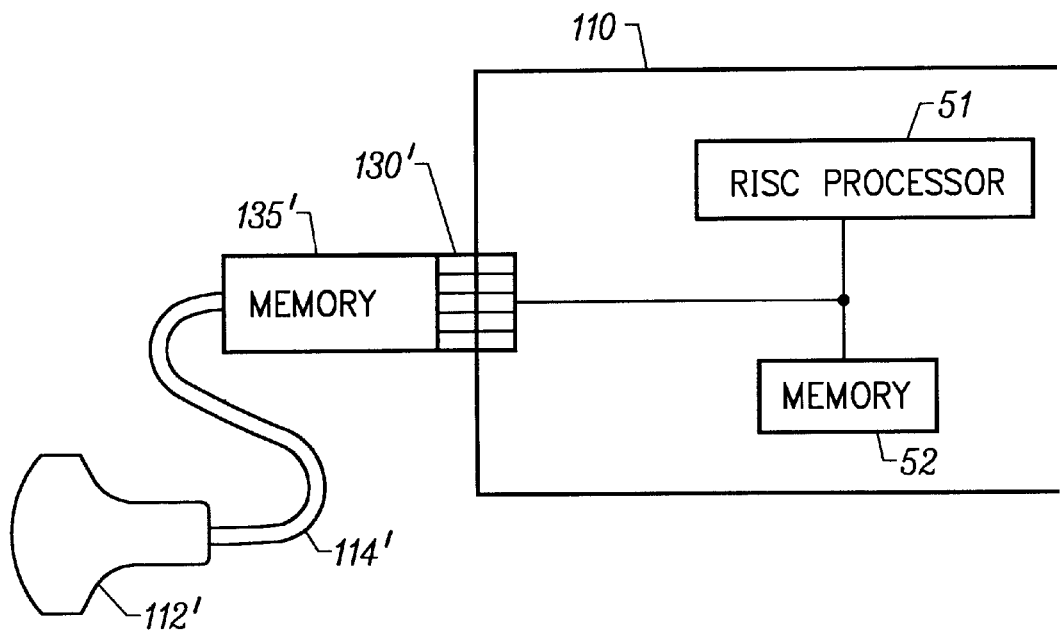
FIG. 3 is a functional block diagram of the ultrasound diagnostic instruments of FIGS. 1 and 2 as modified in accordance with the present invention.
Figure 4:
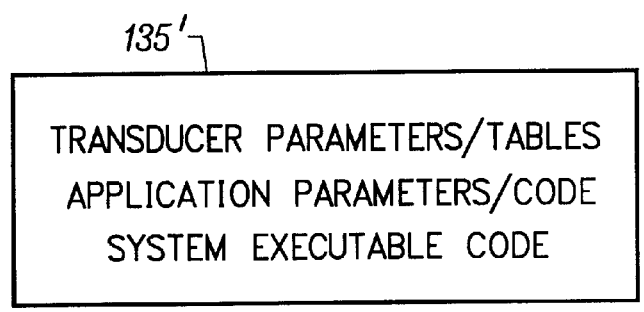
FIG. 4 is a functional block diagram of a memory in an ultrasound diagnostic instrument in accordance with the invention and contents of the memory.

In accordance with the invention, and as shown in FIG. 3 a memory 135' is provided with each scanhead 112' and connector 130' which includes software and data necessary for use of the specific scanhead in the ultrasound diagnostic instrument. The memory can be located in connector 130' in cable 114', or in the scanhead 112'. Cable 114' and connector 130' connect the memory with the processor 51 and memory 52 within module 110. FIG. 4 is a functional block diagram illustrating one embodiment in which the memory 135' is located within connector 130' and interfaces with program memory 52 and RISC processor 51 within module 110. Memory 135' stores operational data unique to a specific transducer scanhead which may be designed for specific applications such as cardiac analysis, neo-natal analysis, gynecology analysis, and prostate analysis. The stored data unique to the scanhead can include signal processing tables and beamforming tables along with filter coefficients, scan conversion coefficients, focusing tables, and compression tables. Calculations necessary for a specific application can also be included.

In addition to transducer scanhead data and application software, the memory can include system executable code which permits update and upgrade of the system executable code resident in memory 52 of the console. Thus software for future applications as well as operational data for various transducer scanheads can be provided in memory without the need for a manual field upgrade of the software stored in the console memory or the need for a system swap when a new function or application is required.

By providing a secondary memory external to the console and in association with a specific transducer scanhead, the memory requirements of the console can be greatly reduced since all the software necessary for a specific function and particular scanheads need not be stored therein. The inclusion of this system executable code obviates the need for field upgrade and provides greater versatility when using a plurality of special purpose transducer scanheads with the ultrasound instrument console. Thus instrument size, weight, and required power are reduced. Further reduction can be provided through use of the instrument as a data gathering instrument with the data being used at a centralized location for imaging. In this connection, memory 135' can include data encryption so that the process signals can be viewed only by an authorized party.

There has been described an ultrasound diagnostic instrument which achieves greater versatility in use by the provision of memory external to an instrument console and in association with a particular transducer scanhead. While the invention has been described with reference to a specific embodiment, the description is illustrative of the invention and is not to be construed as limiting the invention. For example, the memory within the console can be eliminated with the external memory providing all memory functions for the processor as well as the scanhead. Thus, various modifications and applications may occur to those skilled in the art without departing from the true spirit and scope of the invention as defined by the appended claims.

What is claimed is:

1. An ultrasound diagnostic instrument comprising
   a) a console including display electronic circuitry for processing electrical signals for display including a digital processor, a first memory and a first connector coupled to the processor and first memory,
   b) a transducer scanhead for generating ultrasound waves and receiving reflected or scattered ultrasound waves,
   c) means for coupling the transducer scanhead to the console for transmitting electrical signals to and from the scanhead, and
   d) a second memory associated with the scanhead and outside of the console and communicating with the console through a second connector, the second memory storing software and data necessary for use of the transducer scanhead in the ultrasound diagnostic instrument.

2. The ultrasound diagnostic instrument as defined by claim 1 wherein the software and data stored in the second memory include operational data unique to the transducer scanhead.

3. The ultrasound diagnostic instrument as defined by claim 1 wherein the software and data include at least one of physical parameters, operational data for the scanhead, and executable code.

4. The ultrasound diagnostic instrument as defined by claim 1 wherein the software and data include operational software for executing unique functions with the transducer scanhead.

5. The ultrasound diagnostic instrument as defined by claim 4 wherein the operational software provides unique diagnostic analysis.

6. The ultrasound diagnostic instrument as defined by claim 5 wherein the unique diagnostic analysis is selected from a group including cardiac analysis, neo-natal analysis, gynecology analysis and prostate analysis.

7. The ultrasound diagnostic instrument as defined by claim 1 wherein the software and data stored in the second memory includes system executable code for the digital processor.

8. The ultrasound diagnostic instrument as defined by claim 7 wherein the system executable code comprises a software update and upgrade of system executable code in the first memory.

9. The ultrasound diagnostic instrument as defined by claim 8 wherein the system executable code permits new applications of the instrument.

10. The ultrasound diagnostic instrument as defined by claim 8 wherein system executable code permits use of a new transducer scanhead in the instrument.

11. The ultrasound diagnostic instrument as defined by claim 1 wherein the second memory resides in the transducer scanhead.

12. The ultrasound diagnostic instrument as defined by claim 1 wherein the second memory resides in the second connector, the second connector being connected to the means for coupling and mating with the first connector in the console.

13. The ultrasound diagnostic instrument as defined by claim 1 wherein the second memory resides in the means for coupling.

14. The ultrasound diagnostic instrument as defined by claim 1 wherein the console further includes a display for processed electrical signals.

15. The ultrasound diagnostic instrument as defined by claim 1 wherein the console includes internal memory for storing processed electrical signals for display at a remote facility.

16. The ultrasound diagnostic instrument as defined by claim 15 wherein the internal memory includes data encryption for data from the transducer scanhead to the console.

17. The ultrasound diagnostic instrument as defined by claim 1 and further including a console memory within the console for storing software for use with the processor.

18. The ultrasound diagnostic instrument as defined by claim 1 wherein the means for coupling comprises a cable.

19. The ultrasound diagnostic instrument as defined by claim 1 wherein the means for coupling is wireless.

* * * * *